United States Patent
Tanaka et al.

(10) Patent No.: US 10,349,027 B2
(45) Date of Patent: Jul. 9, 2019

(54) IMAGING DEVICE AND PROCESSING DEVICE

(71) Applicant: OLYMPUS CORPORATION, Tokyo (JP)

(72) Inventors: Satoshi Tanaka, Hachioji (JP); Kentaro Hase, Hachioji (JP); Kotaro Ogasawara, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 125 days.

(21) Appl. No.: 15/452,984

(22) Filed: Mar. 8, 2017

(65) Prior Publication Data

US 2017/0180695 A1 Jun. 22, 2017

Related U.S. Application Data

(63) Continuation of application No. PCT/JP2015/074872, filed on Sep. 1, 2015.

(30) Foreign Application Priority Data

Sep. 9, 2014 (JP) .................................. 2014-183390

(51) Int. Cl.
*H04N 9/73* (2006.01)
*A61B 1/04* (2006.01)
(Continued)

(52) U.S. Cl.
CPC .............. *H04N 9/735* (2013.01); *A61B 1/04* (2013.01); *A61B 1/06* (2013.01); *A61B 1/0638* (2013.01);
(Continued)

(58) Field of Classification Search
None
See application file for complete search history.

(56) References Cited

U.S. PATENT DOCUMENTS

2004/0122291 A1* 6/2004 Takahashi ............ A61B 1/0638
600/180
2009/0149706 A1* 6/2009 Yamazaki .............. G02B 23/24
600/109
(Continued)

FOREIGN PATENT DOCUMENTS

JP 2007-097649 A 4/2007
JP 2009-165624 A 7/2009
(Continued)

OTHER PUBLICATIONS

International Search Report dated Nov. 24, 2015 issued in PCT/JP2015/074872.
English Abstract of WO 2013/150897 A1, dated Oct. 10, 2013.

*Primary Examiner* — James M Anderson, II
(74) *Attorney, Agent, or Firm* — Scully, Scott, Murphy & Presser, P.C.

(57) ABSTRACT

An imaging device includes: an imaging unit configured to output an imaging signal; an illumination unit configured to emit respective beams of light of a plurality of colors; a color separation unit configured to separate the imaging signal into a plurality of signals corresponding to the plurality of colors; an interest color setting unit configured to set a color corresponding to a wavelength band of interest as an interest color; a comparison unit configured to compute a ratio between a detection value of a signal corresponding to an interest color set by the interest color setting unit and a detection value of a signal of another color corresponding to a wavelength band different from the wavelength band corresponding to the interest color; and a changing unit configured to change a light emission ratio between light corresponding to the interest color and light of the other color.

6 Claims, 9 Drawing Sheets

(51) Int. Cl.

| | | |
|---|---|---|
| *A61B 1/06* | (2006.01) | |
| *G02B 23/26* | (2006.01) | |
| *G03B 15/02* | (2006.01) | |
| *G03B 15/05* | (2006.01) | |
| *H04N 9/04* | (2006.01) | |
| *G02B 23/24* | (2006.01) | |
| *H04N 5/225* | (2006.01) | |

(52) U.S. Cl.
CPC ..... *G02B 23/2461* (2013.01); *G02B 23/2484* (2013.01); *G02B 23/26* (2013.01); *G03B 15/02* (2013.01); *G03B 15/05* (2013.01); *H04N 5/2256* (2013.01); *H04N 9/04* (2013.01); *H04N 2005/2255* (2013.01)

(56) References Cited

U.S. PATENT DOCUMENTS

2009/0156901 A1\* 6/2009 Gono ................ A61B 1/0638
  600/180
2014/0054450 A1   2/2014 Shirota et al.

FOREIGN PATENT DOCUMENTS

| JP | 2012-029728 A | 2/2012 |
| JP | 2012-125492 A | 7/2012 |
| JP | 2012125492 A \* | 7/2012 |
| JP | 5393935 B1 | 1/2014 |

\* cited by examiner

IMAGING DEVICE AND PROCESSING DEVICE

CROSS-REFERENCE TO RELATED APPLICATIONS

This application is a continuation of PCT international application Ser. No. PCT/JP2015/074872 filed on Sep. 1, 2015 which designates the United States, incorporated herein by reference, and which claims the benefit of priority from Japanese Patent Application No. 2014-183390 filed on Sep. 9, 2014, incorporated herein by reference.

BACKGROUND

1. Technical Field

The disclosure relates to an imaging device including an image sensor having a plurality of pixels and to a processing device connected to the imaging device.

2. Related Art

Conventionally, an endoscope system is used in the medical field when an organ of a subject such as a patient is observed. The endoscope system includes, for example, an endoscope, a light source device, and a processing device. The endoscope has an insertion portion provided with an image sensor at a distal end thereof, and the insertion portion is inserted into a body cavity of the subject. The light source device generates illumination light that is emitted from a distal end of the endoscope. The processing device performs an image process for an in-vivo image corresponding to an imaging signal generated by the image sensor and causes a display unit or the like to display the in-vivo image.

In recent years, as a technique for adjusting a white balance of an image by means of illumination light, a shooting system including a light source unit having a red LED light source that emits light in a red wavelength band, a green LED light source that emits light in a green wavelength band, and a blue LED light source that emits light in a blue wavelength band has been disclosed (for example, refer to JP 2012-29728 A). In JP 2012-29728 A, an object is illuminated with infrared light, and an image obtained by the illumination is subjected to a balance adjustment for RGB signals. Then, light intensity (light quantity) emitted by each of the red LED light source, the green LED light source, and the blue LED light source is individually changed in accordance with the balance, and the white balance of the image obtained by visible light is adjusted.

SUMMARY

In some embodiments, an imaging device includes: an imaging unit configured to capture an imaging object and output an imaging signal; an illumination unit configured to emit respective beams of light of a plurality of colors of wavelength bands different from one another; a color separation unit configured to separate the imaging signal into a plurality of signals corresponding to the plurality of colors; a white balance processing unit configured to multiply each of the plurality of signals separated by the color separation unit by a coefficient to perform a white balance adjustment; an interest color setting unit configured to set a color corresponding to a wavelength band of interest as an interest color; an illumination controller configured to control a light quantity of the interest color; a comparison unit configured to compute a ratio between a detection value of a signal corresponding to an interest color set by the interest color setting unit and a detection value of a signal of another color corresponding to a wavelength band different from the wavelength band corresponding to the interest color among the plurality of signals where each is multiplied by the coefficient by the white balance processing unit; and a changing unit configured to change a light emission ratio between light corresponding to the interest color and light of the other color, based on the ratio computed by the comparison unit, and output, to the illumination controller, a control signal for emitting the respective beams of light of the plurality of colors by the changed light emission ratio.

In some embodiments, a processing device connected to an imaging device and a light source device is provided. The imaging device includes an imaging unit configured to capture an imaging object and output an imaging signal. The light source device is configured to emit respective beams of light of a plurality of colors of wavelength bands different from one another. The processing device is configured to send and receive a signal between the imaging device and the light source device. The processing device includes: a white balance processing unit configured to multiply a plurality of signals by a coefficient to perform a white balance adjustment, the plurality of signals being obtained by separating the imaging signal in accordance with the plurality of colors; an interest color setting unit configured to set a color corresponding to a wavelength band of interest as an interest color; a comparison unit configured to compute a ratio between a detection value of a signal corresponding to an interest color set by the interest color setting unit and a detection value of a signal of another color corresponding to a wavelength band different from the wavelength band corresponding to the interest color among the plurality of signals where each is multiplied by the coefficient by the white balance processing unit; and a changing unit configured to change a light emission ratio between light corresponding to the interest color and light of the other color, based on the ratio computed by the comparison unit, and output, to the illumination controller, a control signal for emitting the respective beams of light of the plurality of colors by the changed light emission ratio.

The above and other features, advantages and technical and industrial significance of this disclosure will be better understood by reading the following detailed description of presently preferred embodiments of the disclosure, when considered in connection with the accompanying drawings.

DETAILED DESCRIPTION

Figure 1:
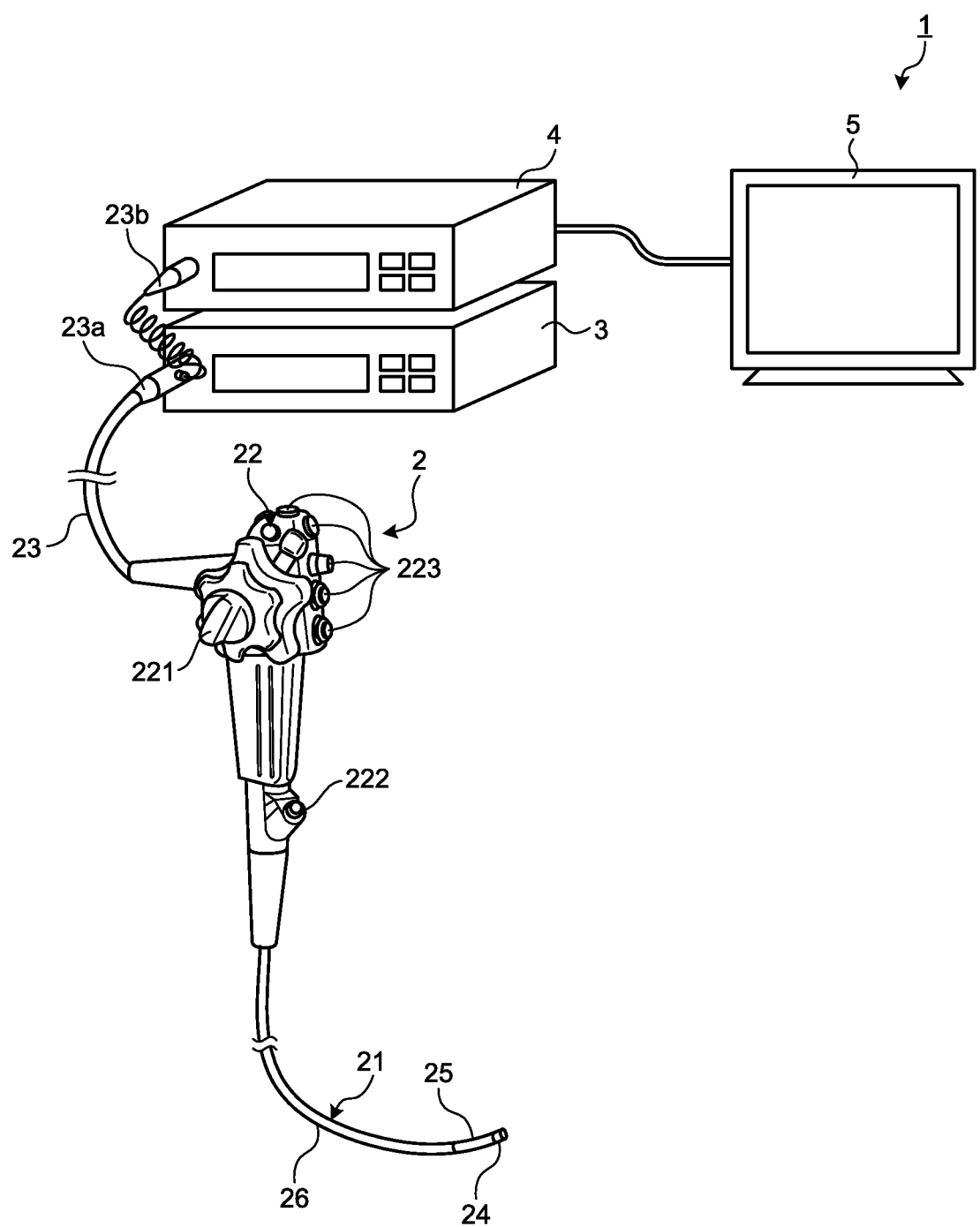
FIG. 1 is a view illustrating a schematic configuration of an endoscope system according to a first embodiment of the disclosure.

Hereinafter, embodiments for practicing the disclosure (hereinafter referred to as "embodiments") will be described. In the embodiments, a medical endoscope system that captures and displays an image within a body cavity of a subject such as a patient is described as an example of a system including an imaging device and a processing device according to the disclosure. The disclosure is not limited by the embodiments. In the drawings, identical elements are provided with the same reference signs for illustration.

First Embodiment

Figure 2:
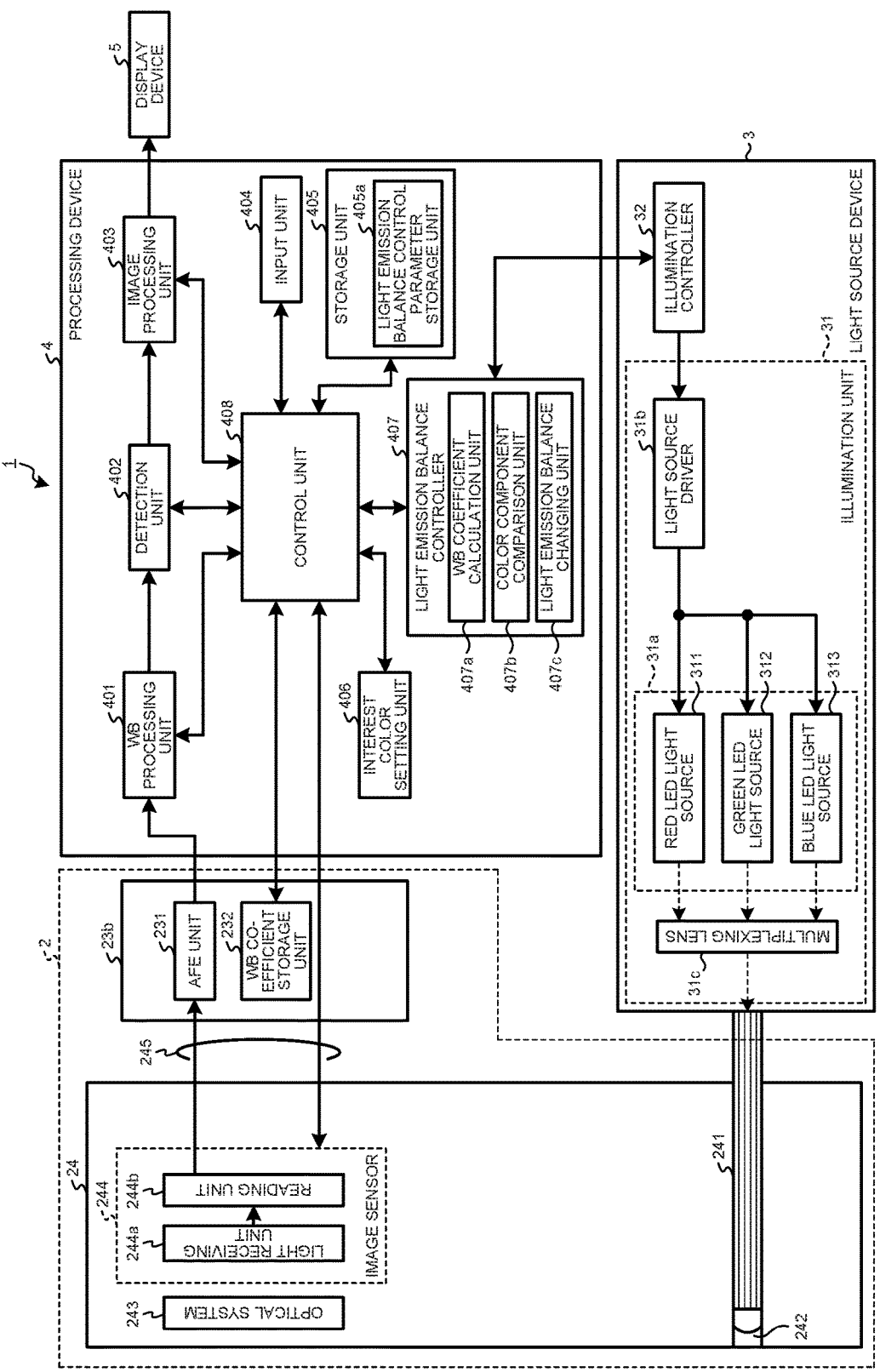
FIG. 2 is a block diagram illustrating the schematic configuration of the endoscope system according to the first embodiment of the disclosure.

FIG. 1 is a view illustrating a schematic configuration of an endoscope system according to a first embodiment of the disclosure. FIG. 2 is a block diagram illustrating the schematic configuration of the endoscope system according to the first embodiment.

An endoscope system 1 illustrated in FIGS. 1 and 2 includes an endoscope 2, a light source device 3, a processing device 4, and a display device 5. A distal end portion of the endoscope 2 is inserted into a body cavity of a subject, whereby the endoscope 2 captures an in-vivo image of the subject. The light source device 3 generates illumination light that is emitted from the distal end of the endoscope 2. The processing device 4 performs a predetermined image process on the in-vivo image captured by the endoscope 2, and comprehensively controls operation of the entire endoscope system 1. The display device 5 displays the in-vivo image subjected to the image process by the processing device 4.

The endoscope 2 includes an insertion portion 21, an operating unit 22, and a universal code 23. The insertion portion 21 has a flexible elongated shape. The operating unit 22 is connected to a proximal end side of the insertion portion 21 to accept input of various operation signals. The universal code 23 extends from the operating unit 22 in a direction different from a direction in which the insertion portion 21 extends. Various cables connected to the light source device 3 and the processing device 4 are incorporated in the universal code 23.

The insertion portion 21 has a distal end portion 24, a curve portion 25, and a flexible pipe portion 26. An image sensor 244 is incorporated in the distal end portion 24. In the image sensor 244, pixels that receive light and perform a photoelectric conversion to generate signals are two-dimensionally arrayed. The curve portion 25 includes a plurality of curve pieces so as to be freely curved. The flexible pipe portion 26 is connected to a proximal end side of the curve portion 25 and has a flexible long shape.

The distal end portion 24 includes a light guide 241, an illumination lens 242, an optical system 243 for collecting light, and the image sensor 244. The light guide 241 includes a glass fiber or the like, and serves as a light guide passage for the light emitted by the light source device 3. The illumination lens 242 is provided at a distal end of the light guide 241. The image sensor 244 is provided at an image forming position of the optical system 243, receives the light collected by the optical system 243, photoelectrically converts the light into an electric signal, and performs a predetermined signal process on the electric signal.

The optical system 243 includes one or more lenses, and has an optical zoom function for changing an angle of view and a focus function for changing a focal point.

The image sensor 244 (imaging unit) photoelectrically converts the light from the optical system 243 to generate the electric signal (imaging signal). More specifically, the image sensor 244 has a light receiving unit 244a and a reading unit 244b. In the light receiving unit 244a, a plurality of pixels is arrayed in a matrix shape. Each of the plurality of pixels has, for example, a photodiode that accumulates a charge that depends on a light quantity and a capacitor that converts the charge transferred from the photodiode into a voltage level. Each pixel photoelectrically converts the light from the optical system 243 to generate the electric signal. The reading unit 244b reads the electric signal generated by each of the plurality of pixels of the light receiving unit 244a, and outputs the electric signal as an imaging signal. A color filter is provided in each pixel of the light receiving unit 244a. Therefore, each pixel receives the light in a wavelength band transmitted through the color filter (for example, red light, green light, or blue light), and accumulates the charge that depends on the received light. The image sensor 244 controls various types of operation of the distal end portion 24 in accordance with a drive signal received from the processing device 4. The image sensor 244 is realized with the use of, for example, a charge coupled device (CCD) image sensor or a complementary metal oxide semiconductor (CMOS) image sensor.

The operating unit 22 has a curve knob 221, a treatment tool insertion portion 222, and a plurality of switches 223. The curve knob 221 curves the curve portion 25 in an up-down direction and a left-right direction. A treatment tool such as living body forceps, an electric scalpel, and an examination probe is inserted into the body cavity of the subject through the treatment tool insertion portion 222. The plurality of switches 223 serves as an operation input unit through which an operation instruction signal for a peripheral device such as an air supply unit, a water supply unit, and screen display control as well as the processing device 4 and the light source device 3 is input. The treatment tool inserted through the treatment tool insertion portion 222 passes through a treatment tool channel (not illustrated) of the distal end portion 24 and comes out of an opening portion (not illustrated).

The light guide 241 and an aggregated cable 245 are at least incorporated in the universal code 23. One or more signal lines are bundled in the aggregated cable 245. The aggregated cable 245 includes a signal line for sending and receiving setting data, a signal line for sending and receiving the imaging signal, and a signal line for sending and receiving a drive timing signal for driving the image sensor 244.

The universal code 23 has a connector unit 23a connected to the light source device 3 and a connector unit 23b connected to the processing device 4. The connector unit 23b has an AFE unit 231 and a white balance (WB) coefficient storage unit 232.

The AFE unit 231 (color separation unit) has, for example, a noise reduction circuit, an automatic gain control (AGC) circuit, an A/D conversion circuit, and a color separation circuit. The noise reduction circuit reduces a noise component included in the analog imaging signal using a correlated double sampling (CDS) method. The AGC circuit adjusts an amplification factor (gain) of the electric signal to maintain a fixed output level. The A/D conversion circuit performs an A/D conversion on the imaging signal output through the AGC circuit. The color separation circuit separates the signal in accordance with color components of the color filters provided in the light receiving unit 244a. For example, in a case where the color filters include red (R), green (G), and blue (B), the color separation circuit refers to the arrangement of the color filters and the pixels, and performs the separation into a red (R) signal, a green (G) signal, and a blue (B) signal (separation signals). The AFE unit 231 performs the signal process on the imaging signal output from the reading unit 244b by means of the above-mentioned circuits, and thereafter outputs the imaging signal subjected to the signal process to the processing device 4.

The WB coefficient storage unit 232 is realized with the use of a flash memory or the like. The WB coefficient storage unit 232 stores a WB coefficient that is a coefficient for adjusting a white balance. The WB coefficient includes a plurality of coefficients by which the R signal, the G signal, and the B signal set in accordance with the image sensor 244 are multiplied. For example, each coefficient computed at the time of calibration is stored as the WB coefficient. In addition, identification information related to the endoscope 2 (for example, unique information (ID), a model year, and specification information or the like of the endoscope 2) may be stored.

Next, a configuration of the light source device 3 will be described. The light source device 3 includes an illumination unit 31 and an illumination controller 32.

Under the control of the illumination controller 32, the illumination unit 31 sequentially switches between a plurality of beams of illumination light in different wavelength bands, and emits the plurality of beams of light to an object (subject). The illumination unit 31 includes a light source unit 31a, a light source driver 31b, and a multiplexing lens 31c.

The light source unit 31a includes a red LED light source 311, a green LED light source 312, and a blue LED light source 313 as well as one or more lenses or the like. Each LED light source emits light in the corresponding wavelength band under the control of the light source driver 31b. The illumination light generated by the light source unit 31a passes through the light guide 241 and is emitted from a distal end of the distal end portion 24 to the object. More specifically, the light source unit 31a causes each of the red LED light source 311, the green LED light source 312, and the blue LED light source 313 to emit the light, whereby the light including the respective wavelength bands of the red light, the green light, and the blue light (for example, red: 600 nm to 700 nm, green: 500 nm to 600 nm, blue: 400 nm to 500 nm) is emitted as the illumination light. Consequently, the illumination unit 31 can sequentially emit any of the red light (R illumination), the green light (G illumination), and the blue light (B illumination) to the endoscope 2 by means of the light source unit 31a (frame sequential method).

The light source driver 31b causes the light source unit 31a to emit the illumination light by supplying a current to each of the red LED light source 311, the green LED light source 312, and the blue LED light source 313 of the light source unit 31a under the control of the illumination controller 32.

The multiplexing lens 31c collects the beams of light in the respective wavelength bands emitted from the red LED light source 311, the green LED light source 312, and the blue LED light source 313, multiplexes the beams of light in these wavelength bands, and emits the light as the illumination light (for example, white light).

The illumination controller 32 controls the wavelength band and the light quantity of the illumination light emitted by the illumination unit 31 by controlling the light source driver 31b to turn on/off the red LED light source 311, the green LED light source 312, and the blue LED light source 313 of the light source unit 31a. Based on a signal from the processing device 4, the illumination controller 32 controls the amount of power supplied by the light source driver 31b to the light source unit 31a (each LED light source), and controls the drive timing (light emission period) at which the light source driver 31b drives the light source unit 31a.

Next, a configuration of the processing device 4 will be described. The processing device 4 includes a white balance (WB) processing unit 401, a detection unit 402, an image processing unit 403, an input unit 404, a storage unit 405, an interest color setting unit 406, a light emission balance controller 407, and a control unit 408.

The WB processing unit 401 performs a white balance adjustment on the R signal, the G signal, and the B signal included in the imaging signal output from the endoscope 2 (AFE unit 231), and outputs the imaging signal (the R signal, the G signal, and the B signal) subjected to the white balance adjustment to the detection unit 402. More specifically, the WB processing unit 401 acquires, from the light emission balance controller 407 or the WB coefficient storage unit 232, the white balance coefficient for the signal of each color component, and multiplies the signal of each color component by the corresponding coefficient to perform the white balance adjustment.

The detection unit 402 detects a signal value (luminance value of each pixel) after the white balance adjustment from each of the R signal, the G signal, and the B signal input from the WB processing unit 401, and outputs the signal value of each color component as a detection value. The detection unit 402 also outputs, to the image processing unit 403, the imaging signal (the R signal, the G signal, and the B signal) subjected to the white balance adjustment and output from the WB processing unit 401. The detection unit 402 may output an average value of the luminance values of the identical color components as the detection value, or may output the maximum value, the minimum value, the most frequent value or the like as the detection value.

The image processing unit 403 generates the in-vivo image that is displayed by the display device 5 based on the imaging signal input from the detection unit 402. The image processing unit 403 executes a predetermined image process on the imaging signal to generate an in-vivo image signal including the in-vivo image. Examples of the image process include a synchronization process, an optical black subtraction process, a white balance adjustment process, a color matrix calculation process, a gamma correction process, a color reproduction process, an edge enhancement process, a combining process for combining a plurality of pieces of image data, and a format conversion process or the like.

The input unit 404 accepts input of various signals such as an instruction signal for giving an instruction for the operation of the endoscope system 1.

The storage unit 405 is realized with the use of a semiconductor memory such as a flash memory and a dynamic random access memory (DRAM). The storage unit 405 stores data including, for example, various programs for operating the endoscope system 1 and various parameters required for the operation of the endoscope system 1. The storage unit 405 also stores identification information of the processing device 4. Examples of the identification information include unique information (ID), a model year, specification information, a transmission method, and a transmission rate or the like of the processing device 4.

The storage unit 405 has a light emission balance control parameter storage unit 405a that stores a WB gain threshold value (first threshold value) that is a threshold value of a ratio of the white balance coefficient of each color component and a detection threshold value of the detection value provided by the detection unit 402 (threshold value of a ratio of the signal value of each color, i.e. a second threshold value). The WB gain threshold values and the detection threshold values are set for the respective color components of the R signal, the G signal, and the B signal, and stored in the light emission balance control parameter storage unit 405a.

The interest color setting unit 406 sets a color of interest based on the instruction signal accepted by the input unit 404. More specifically, the interest color setting unit 406 sets the interest color to red in response to the instruction signal for employing red as the interest color being input through the input unit 404.

The light emission balance controller 407 generates a control signal for driving each LED light source of the light source unit 31a, and outputs the control signal to the illumination controller 32. The light emission balance controller 407 has a WB coefficient calculation unit 407a, a color component comparison unit 407b, and a light emission balance changing unit 407c.

The WB coefficient calculation unit 407a calculates the WB coefficient of the color component set by the interest color setting unit 406 with reference to the WB gain threshold value stored in the light emission balance control parameter storage unit 405a. More specifically, the WB coefficient calculation unit 407a computes a gain ratio based on the WB coefficient of each color, compares the gain ratio with the WB gain threshold value, and reduces the gain ratio when the gain ratio of the interest color is greater than the WB gain threshold value. The WB coefficient calculation unit 407a calculates the WB coefficient based on the gain ratio subjected to the subtraction. Consequently, the coefficient of the interest color related to the white balance is changed. The WB coefficient calculation unit 407a outputs the WB coefficient subjected to the calculation to the WB coefficient storage unit 232 and the WB processing unit 401.

The color component comparison unit 407b acquires the detection values of the R signal, the G signal, and the B signal from the detection unit 402, and compares existence ratios of the component of the interest color and the components of the other colors in the object (imaging signal). More specifically, the color component comparison unit 407b computes detection value ratios from the acquired detection values, acquires the detection threshold value of the interest color from the light emission balance control parameter storage unit 405a, and determines whether the detection value ratio of the interest color is greater than the detection threshold value. The color component comparison unit 407b outputs, to the light emission balance changing unit 407c, the determination result associated with the detection value ratio of the interest color.

The light emission balance changing unit 407c performs control to change a light emission balance in accordance with the calculation result of the WB coefficient calculation unit 407a and the determination result of the color component comparison unit 407b. The light emission balance changing unit 407c changes the light quantity of the LED light source corresponding to the interest color when the light emission balance changing unit 407c determines to change the light emission balance with reference to the calculation result and the determination result. The light emission balance changing unit 407c outputs, to the illumination controller 32, a control signal for emitting the illumination light in the changed light emission balance.

The control unit 408 includes a central processing unit (CPU) or the like, and performs drive control on the respective components including the endoscope 2 and the light source device 3 and information input/output control on the respective components. The control unit 408 sends the setting data for imaging control (for example, imaging timing or the like) stored in the storage unit 405 to the image sensor 244 through the predetermined signal line included in the aggregated cable 245.

The display device 5 receives and displays the in-vivo image corresponding to the in-vivo image signal generated by the processing device 4 through a video cable. The display device 5 includes liquid crystal or organic electro luminescence (EL).

In the first embodiment, the imaging device includes the image sensor 244, the AFE unit 231, the illumination unit 31, the illumination controller 32, the interest color setting unit 406, and the light emission balance controller 407.

Figure 3:
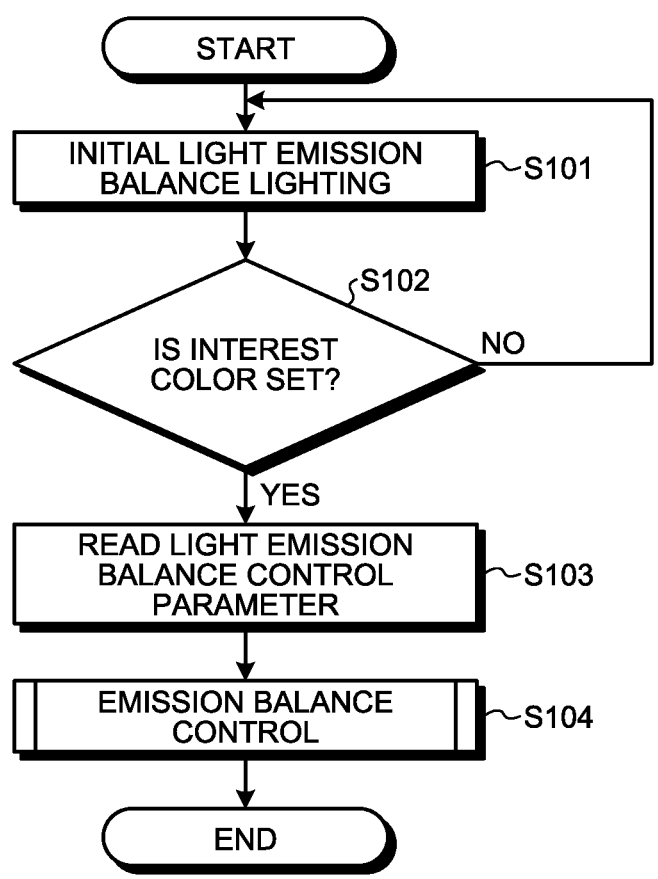
FIG. 3 is a flowchart illustrating a light emission control process performed by the endoscope system according to the first embodiment of the disclosure.

Next, the light emission control performed by the endoscope system 1 will be described with reference to FIG. 3. FIG. 3 is a flowchart illustrating the light emission control process performed by the endoscope system according to the first embodiment of the disclosure. First, the light emission balance controller 407 controls the illumination controller 32 to turn on the illumination light in an initial light emission balance (step S101). The initial light emission balance as used herein is a state free from the interest color setting of the interest color setting unit 406, namely, for example, a normal white balance adjusted to produce the white color. The illumination controller 32 controls the light quantity emitted from each LED light source so that the white illumination light is produced in accordance with the normal white balance, and causes the illumination light to be emitted from the multiplexing lens 31c.

After that, the light emission balance controller 407 determines whether the interest color is set by the interest color setting unit 406 (step S102). When the interest color is not set by the interest color setting unit 406 (step S102: No), the light emission balance controller 407 returns to step S101 and performs the control to emit the illumination light in the normal white balance.

On the other hand, when the interest color is set by the interest color setting unit 406 (step S102: Yes), the light emission balance controller 407 reads a light emission balance control parameter (the WB gain threshold value and the detection threshold value) corresponding to the interest color (step S103).

In response to reading the light emission balance control parameter, the light emission balance controller 407 changes the light emission balance based on the read light emission balance control parameter, and controls the illumination controller 32 so that the illumination light is emitted in the changed light emission balance (step S104).

Figure 4:
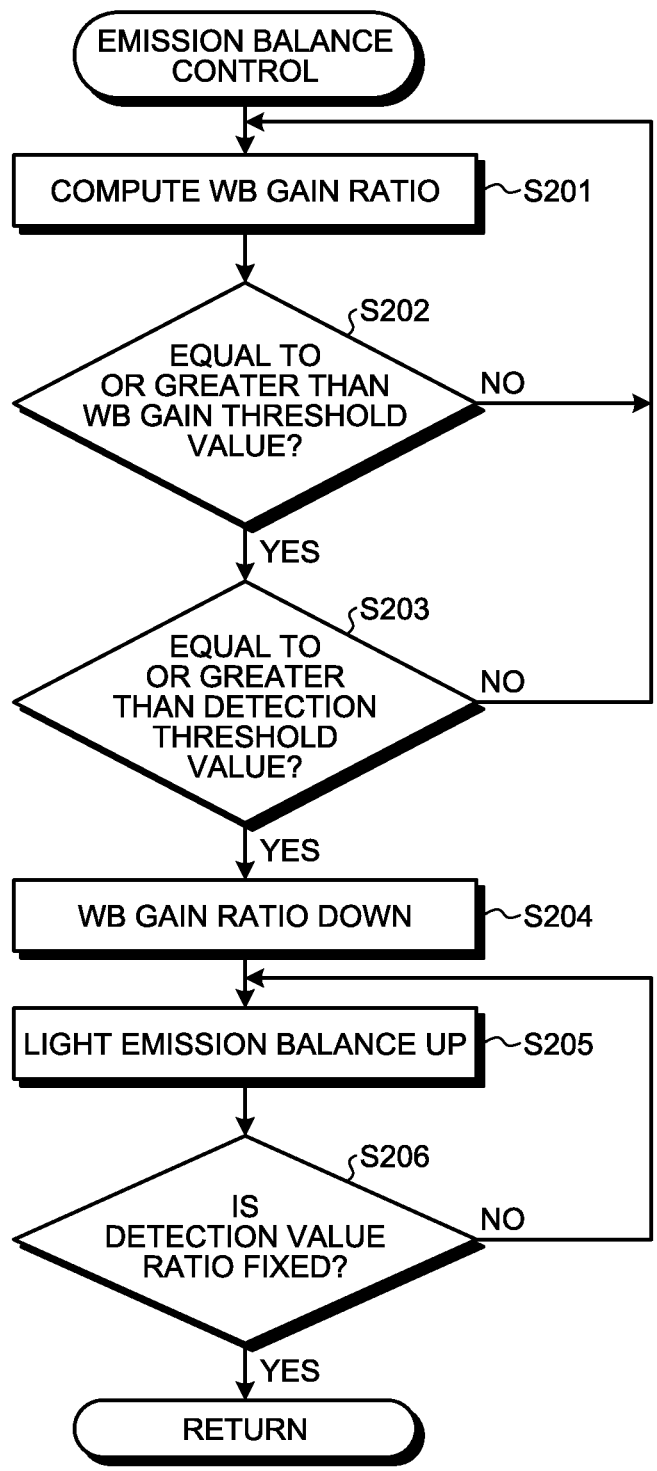
FIG. 4 is a flowchart illustrating a light emission balance control process performed by a light emission balance controller of the endoscope system according to the first embodiment of the disclosure.

Next, the light emission balance control performed by the endoscope system 1 will be described with reference to FIGS. 4 to 10. FIG. 4 is a flowchart illustrating the light emission balance control process performed by the light emission balance controller according to the first embodiment.

In the light emission balance control process, first, the WB coefficient calculation unit 407a acquires the WB coefficients (gains) and computes the gain ratios (WB gain ratios) based on the WB coefficients of the respective colors (step S201). More specifically, for example, using the WB coefficient of the green signal value (G signal) as a standard (for example, one), the ratios of the WB coefficients of the other colors are computed. After computing the WB gain ratios, the WB coefficient calculation unit 407a compares the WB gain ratio of the interest color and the WB gain threshold value, and determines whether the WB gain ratio is equal to or greater than the WB gain threshold value (step S202).

Figure 5:
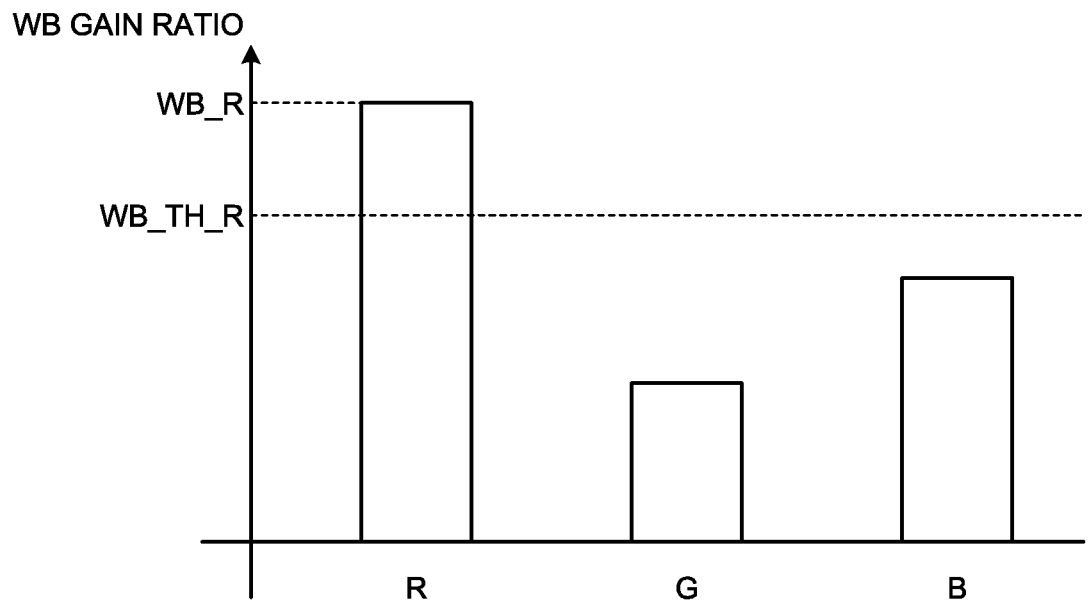
FIG. 5 is a diagram explaining a WB gain ratio computation process of the light emission balance control process performed by the light emission balance controller of the endoscope system according to the first embodiment of the disclosure.

FIG. 5 is a diagram explaining the WB gain ratio computation process of the light emission balance control process performed by the light emission balance controller of the endoscope system according to the first embodiment. For example, when the interest color is red (R), and the WB gain ratios illustrated in FIG. 5 are obtained in step S201, the WB coefficient calculation unit 407a determines that the R gain ratio WB_R is greater than the WB gain threshold value WB_TH_R. When the WB gain ratio of the interest color is equal to or greater than the WB gain threshold value, it can be determined that the sensitivity of the interest color is low. When it is determined by the WB coefficient calculation unit 407a that the WB gain ratio of the interest color is equal to or greater than the WB gain threshold value (step S202: Yes), the light emission balance controller 407 causes the color component comparison unit 407b to perform the process of comparing the detection value ratios (step S203).

Figure 6:
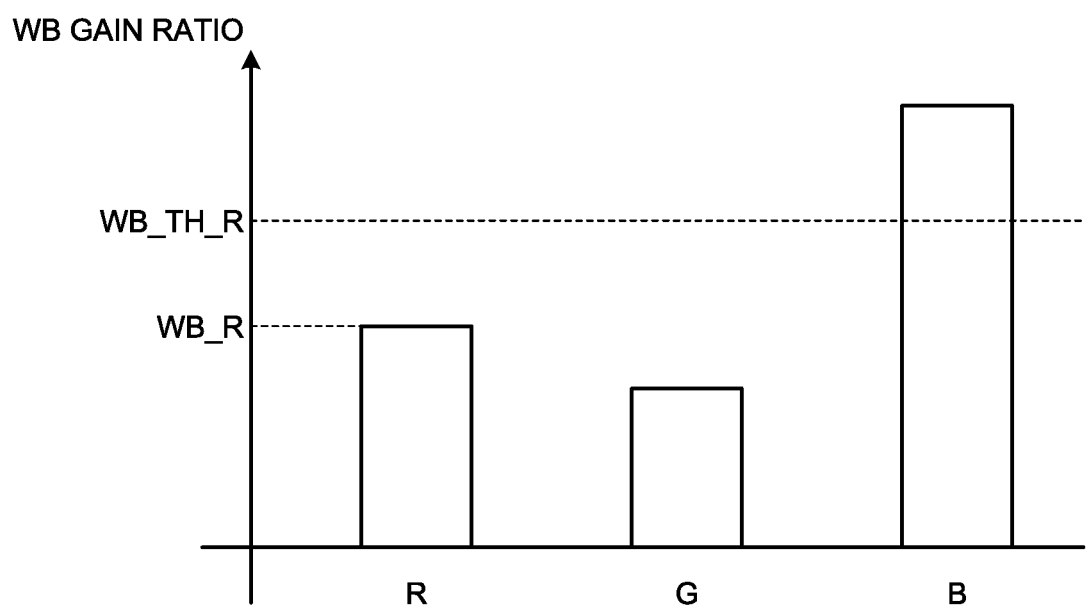
FIG. 6 is a diagram explaining the WB gain ratio computation process of the light emission balance control process performed by the light emission balance controller of the endoscope system according to the first embodiment of the disclosure.

FIG. 6 is a diagram explaining the WB gain ratio computation process of the light emission balance control process performed by the light emission balance controller of the endoscope system according to the first embodiment. For example, when the interest color is red (R), and the WB gain ratios illustrated in FIG. 6 are obtained in step S201, the WB coefficient calculation unit 407a determines that the R gain ratio WB_R is less than the WB gain threshold value WB_TH_R. When the WB gain ratio of the interest color is less than the WB gain threshold value according to the WB coefficient calculation unit 407a, it can be determined that the sensitivity of the interest color is high. When the WB coefficient calculation unit 407a determines that the WB gain ratio is less than the WB gain threshold value (step S202: No), the WB coefficient calculation unit 407a returns to step S201.

Figure 7:
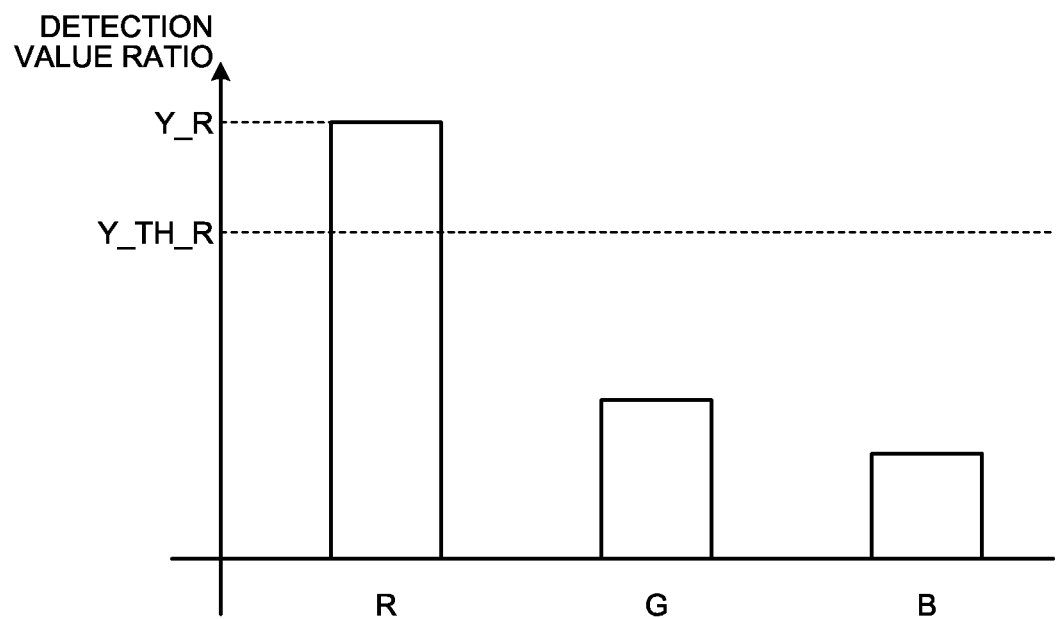
FIG. 7 is a diagram explaining a detection value comparison process of the light emission balance control process performed by the light emission balance controller of the endoscope system according to the first embodiment of the disclosure.

FIG. 7 is a diagram explaining the detection value comparison process of the light emission balance control process performed by the light emission balance controller of the endoscope system according to the first embodiment. In step S203, the color component comparison unit 407b acquires the detection values of the R signal, the G signal, and the B signal from the detection unit 402, computes the detection value ratios from the acquired detection values, and determines whether the detection value ratio of the interest color is greater than the detection threshold value. For example, when the interest color is red (R), and the detection value ratios illustrated in FIG. 7 are obtained, the color component comparison unit 407b determines that the R detection value ratio Y_R is greater than the detection threshold value Y_TH_R. When the detection value ratio of the interest color is equal to or greater than the detection threshold value, it can be determined that the existence ratio of the interest color in the object is high. When the color component comparison unit 407b determines that the detection value ratio of the interest color is equal to or greater than the detection threshold value (step S203: Yes), the light emission balance controller 407 causes the WB coefficient calculation unit 407a to perform the process of changing the WB gain ratio of the interest color (step S204).

Figure 8:
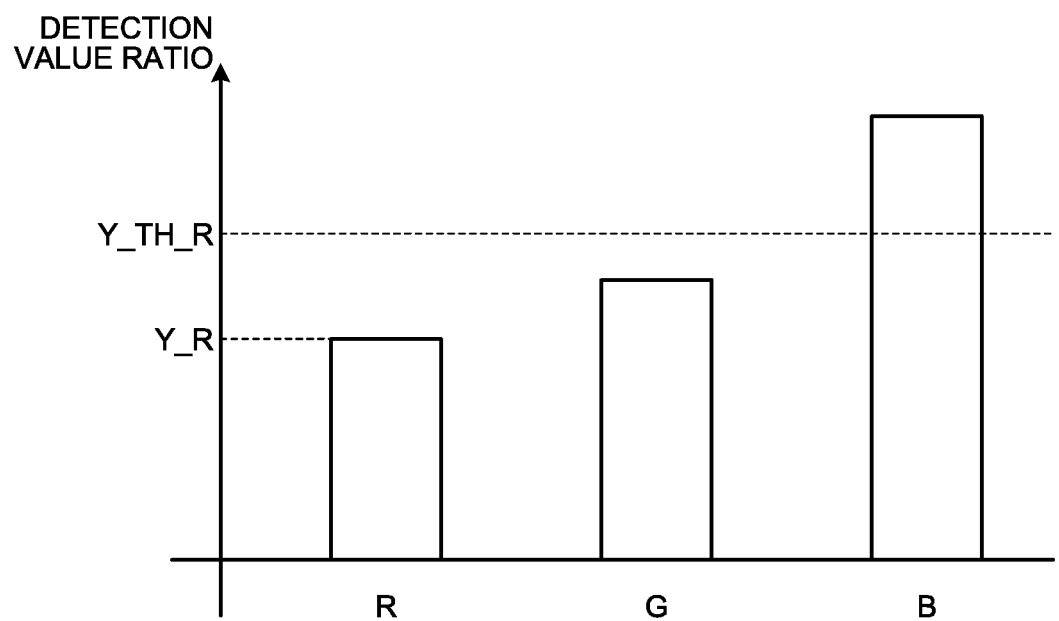
FIG. 8 is a diagram explaining a detection value comparison process of the light emission balance control process performed by the light emission balance controller of the endoscope system according to the first embodiment of the disclosure.

FIG. 8 is a diagram explaining the detection value comparison process of the light emission balance control process performed by the light emission balance controller of the endoscope system according to the first embodiment of the disclosure. For example, when the interest color is red (R), and the detection value ratios illustrated in FIG. 8 are obtained, the color component comparison unit 407b determines that the R detection value ratio Y_R is less than the detection threshold value Y_TH_R. When the detection value ratio of the interest color is less than the detection threshold value, it can be determined that the existence ratio of the interest color in the object is low. When the color component comparison unit 407b determines that the detection value ratio of the interest color is less than the detection threshold value (step S203: No), the color component comparison unit 407b returns to step S201.

Returning to the flowchart in FIG. 4, when it is determined that the WB gain ratio of the interest color is equal to or greater than the WB gain threshold value, and the detection value ratio of the interest color is equal to or greater than the detection threshold value, that is, when it is determined that the sensitivity of the interest color is low, and the existence ratio of the interest color in the object is high, the WB coefficient calculation unit 407a performs the process of changing the WB gain ratio of the interest color (WB gain ratio down process) (step S204).

Figure 9:
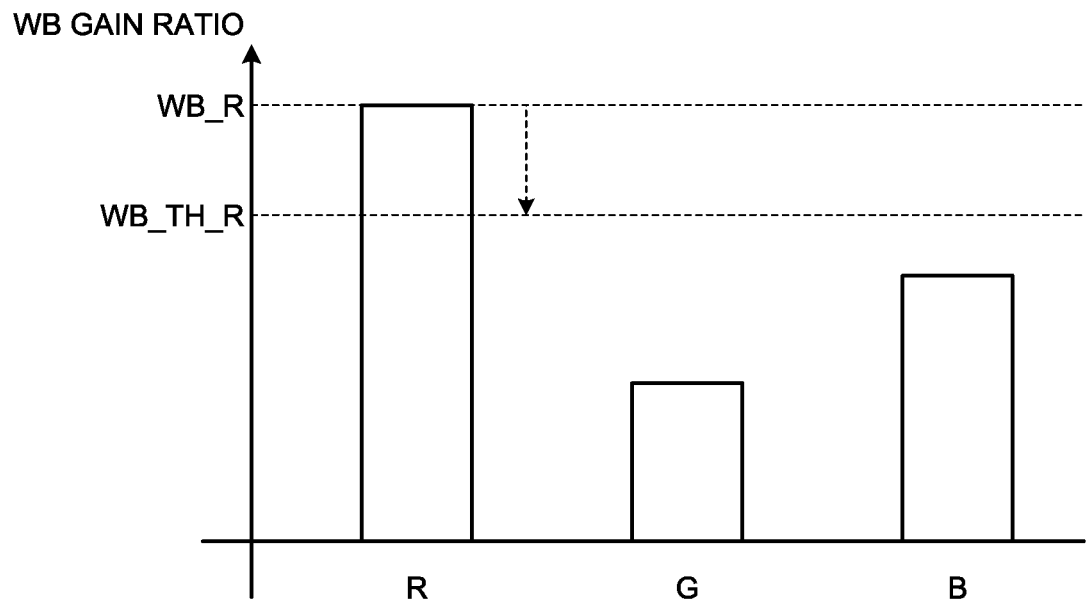
FIG. 9 is a diagram explaining a WB gain ratio down process of the light emission balance control process performed by the light emission balance controller of the endoscope system according to the first embodiment of the disclosure.

FIG. 9 is a diagram explaining the WB gain ratio down process of the light emission balance control process performed by the light emission balance controller of the endoscope system according to the first embodiment. The WB coefficient calculation unit 407a reduces the WB gain ratio so that the gain ratio WB_R of the interest color is equal to the WB gain threshold value WB_TH_R. The WB coefficient calculation unit 407a calculates the WB coefficient based on the gain ratio subjected to the subtraction.

Figure 10:
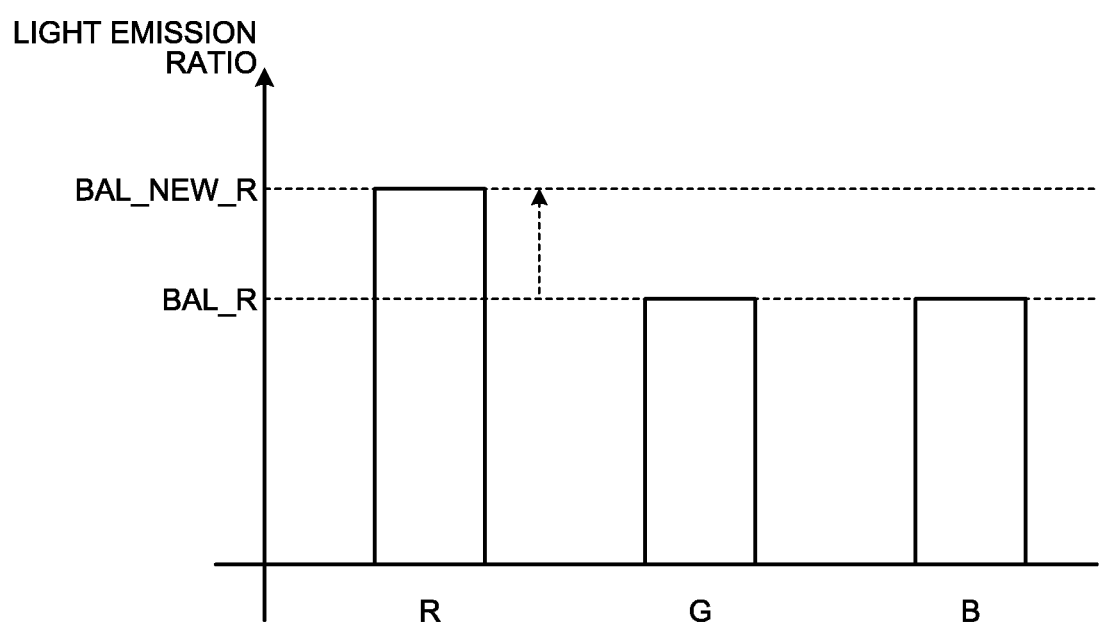
FIG. 10 is a diagram explaining a light emission balance up process of the light emission balance control process performed by the light emission balance controller of the endoscope system according to the first embodiment of the disclosure.

After the WB gain ratio down process performed by the WB coefficient calculation unit 407a, the light emission balance changing unit 407c performs the process of changing the light emission balance (light emission balance up process) (step S205). FIG. 10 is a diagram explaining the light emission balance up process of the light emission balance control process performed by the light emission balance controller of the endoscope system according to the first embodiment. The light emission balance changing unit 407c changes a light emission ratio of the LED light source of the interest color. For example, when the interest color is red (R), as illustrated in FIG. 10, the light emission ratio BAL_R of the red LED light source 311 before the change is increased to the light emission ratio BAL_NEW_R. In this case, the light emission balance changing unit 407c increases the light emission ratio by a preset amount.

After that, the light emission balance controller 407 instructs the illumination controller 32 to emit the illumination light using the new light emission ratio computed by the light emission balance changing unit 407c. The illumination controller 32 controls the red LED light source 311, the green LED light source 312, and the blue LED light source 313 to perform the control to emit the illumination light in the newly set light emission balance. The light emission balance controller 407 acquires the imaging signal (the R signal, the G signal, and the B signal) obtained through use of the new light emission ratio, and causes the color component comparison unit 407b to determine whether the detection value ratio of the interest color is fixed with respect to the detection value ratio before the change (step S206).

The color component comparison unit 407b acquires the imaging signal (the R signal, the G signal, and the B signal) obtained through use of the new light emission ratio, computes the detection value ratios from the detection values that are based on the acquired imaging signal, and determines whether the detection value ratio of the interest color is fixed with respect to the detection value ratio before the change of the light emission ratio. For example, the color component comparison unit 407b determines whether the detection value ratio subjected to the change of the light emission ratio coincides with the detection value ratio Y_R illustrated in FIG. 7. When it is determined by the color component comparison unit 407b that the detection value ratio of the interest color is fixed with respect to the detection value ratio before the change of the light emission ratio (step S206: Yes), the light emission balance controller 407 finishes the light emission balance control process.

On the other hand, when it is determined by the color component comparison unit 407b that the detection value ratio of the interest color is not fixed with respect to the detection value ratio before the change of the light emission ratio (step S206: No), the light emission balance controller 407 returns to step S205 and repeats the light emission balance up process.

When the above-mentioned light emission control process is performed, the initial light emission balance lighting in step S101 is performed at the time of starting the device (at the time of the first light emission control process). In the second and subsequent light emission control processes, the initial light emission balance lighting may be performed, or whether the interest color is set or not may be confirmed without the initial light emission balance lighting, and the processes in step S103 and subsequent steps may be performed.

According to the above-mentioned first embodiment, the light emission balance controller 407 adjusts the light emission balance by increasing only the light emission ratio of the interest color based on the light emission balance control parameter (the WB gain threshold value and the detection threshold value) corresponding to the interest color. Therefore, the amount of heat generation can be suppressed, and the light quantity of the color component of interest can be increased.

In addition, according to the above-mentioned first embodiment, owing to the above-mentioned light emission balance control process, the WB coefficient of the interest color can be reduced, and the light quantity of the LED light source of the interest color can be increased so that the detection value ratio is fixed with respect to the detection value ratio before the change. Therefore, the WB coefficient can be reduced to suppress a factor of noise amplification, and the light quantity of only the specific color component can be increased.

The description has been provided on the premise that the light emission balance changing unit 407c increases the light emission ratio by the preset amount. However, the light emission balance changing unit 407c may acquire the subtraction amount for the WB gain ratio from the WB coefficient calculation unit 407a and increase the light emission ratio in accordance with the subtraction amount.

The first embodiment has been described on the premise that the AFE unit 231 has the function of the color separation unit. However, a color separation unit independent of the AFE unit 231 may be provided, or the color separation unit may be provided in the processing device 4.

The first embodiment has been described on the premise that the connector unit 23b has the AFE unit 231 and the WB coefficient storage unit 232. However, the AFE unit 231 and the WB coefficient storage unit 232 may be provided in a proximal end part of the universal code 23 close to the operating unit 22 or provided in the operating unit 22.

Second Embodiment

Figure 11:
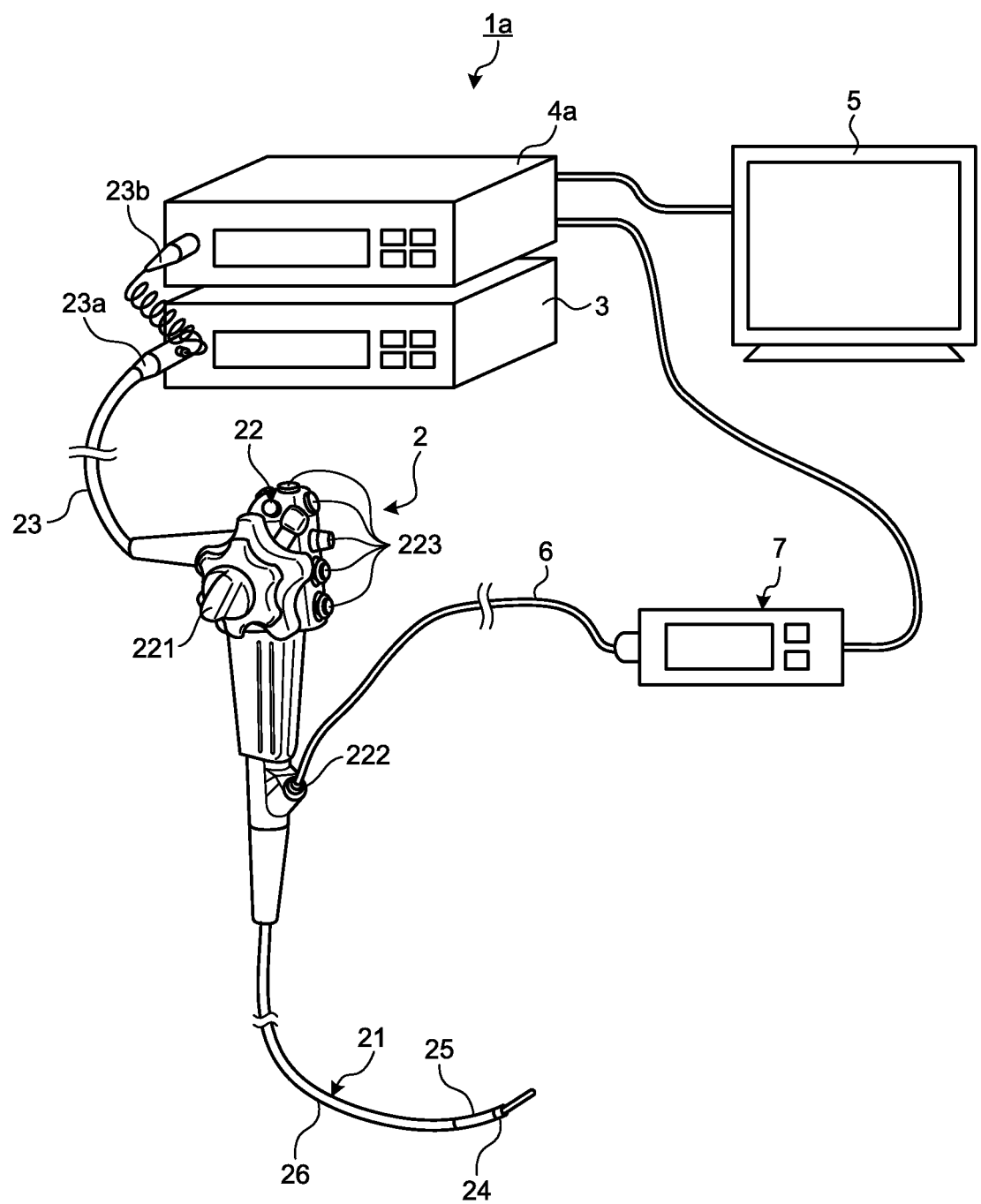
FIG. 11 is a view illustrating a schematic configuration of an endoscope system according to a second embodiment of the disclosure.
Figure 12:
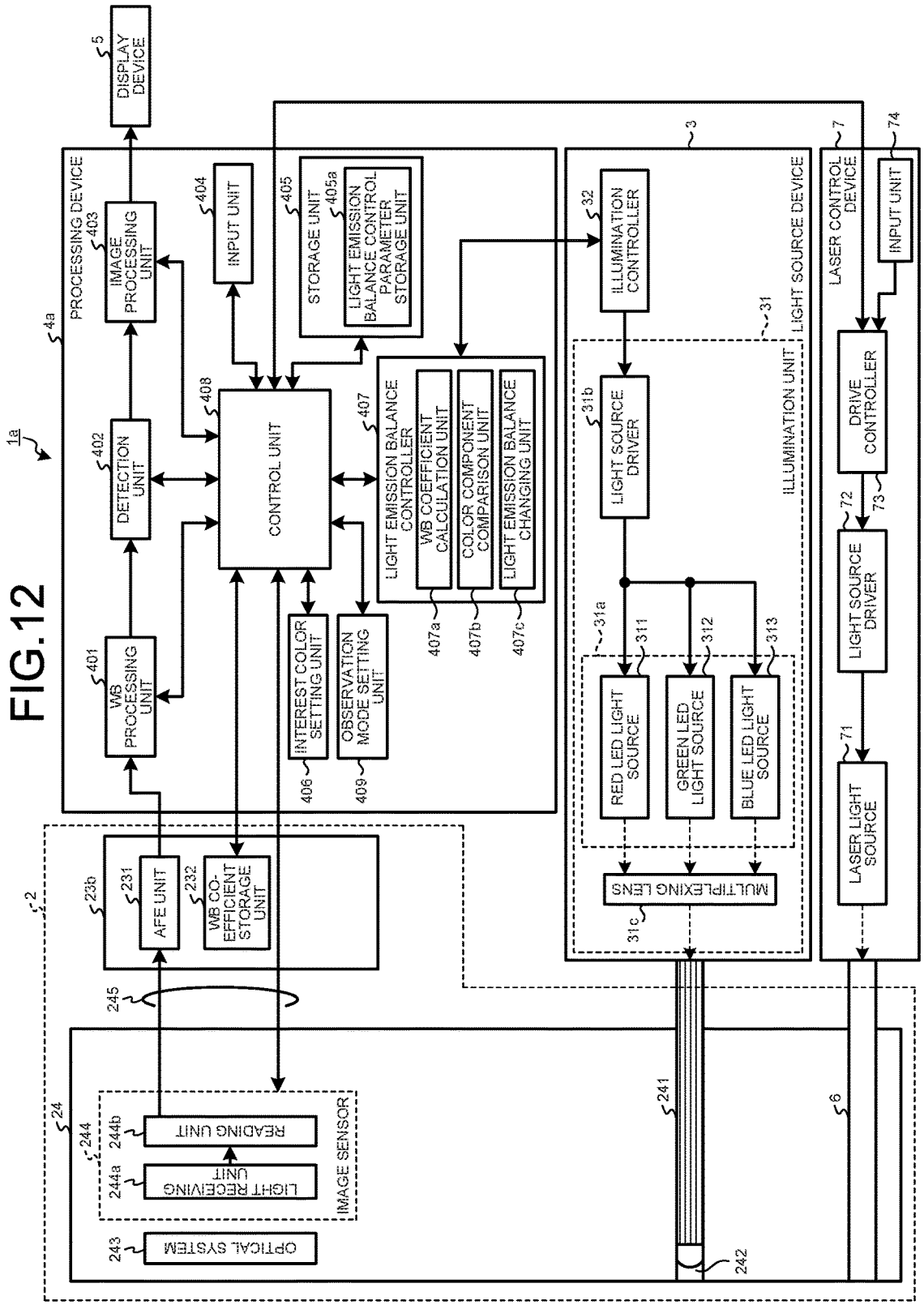
FIG. 12 is a block diagram illustrating the schematic configuration of the endoscope system according to the second embodiment of the disclosure.

Next, a second embodiment of the disclosure will be described. FIG. 11 is a view illustrating a schematic configuration of an endoscope system according to the second embodiment. FIG. 12 is a block diagram illustrating the schematic configuration of the endoscope system according to the second embodiment. Components identical to the above-mentioned components are provided with the same reference signs for illustration. In comparison with the configuration of the endoscope system 1 according to the above-mentioned first embodiment, an endoscope system 1a according to the second embodiment is configured such that a processing device 4a corresponding to the processing device 4 has an observation mode setting unit 409. The endoscope system 1a further includes a probe 6 capable of emitting a laser and a laser control device 7 connected to the probe 6 to supply laser light to the probe 6. The probe 6 and the laser control device 7 constitute a laser device.

The observation mode setting unit 409 changes an observation mode in accordance with a signal input from the laser control device 7. More specifically, when the signal is not input from the laser control device 7, the observation mode is set to a normal observation mode, and the signal process or the like is performed in accordance with the configuration of the above-mentioned first embodiment. To the contrary, when the signal is input from the laser control device 7, the observation mode is set to a laser light observation mode, and the above-mentioned interest color is set to the color component corresponding to the wavelength band of the laser light, whereby the signal process or the like is performed.

The probe 6 is inserted into the treatment tool insertion portion 222 of the endoscope 2 and comes out of the distal end portion 24. The inside of the probe 6 is provided with a fiber that guides the laser light and a lens or the like, and the probe 6 emits the laser light from the fiber through the lens or the like. A proximal end surface of the probe 6 is connected to a laser light emission surface of the laser control device 7. For example, an observed region within the body is irradiated with the laser light using the probe 6, whereby a treatment such as incision, blood stanching, clotting, and evaporation is performed on a living body tissue.

The laser control device 7 has a laser light source 71, a light source driver 72, a drive controller 73, and an input unit 74. The laser light source 71 is realized with the use of a solid-state laser or a semiconductor laser. The light source driver 72 causes the laser light source 71 to emit the laser light by supplying a current to the laser light source 71 under the control of the drive controller 73. The drive controller 73 controls the laser light emitted by the laser control device 7 by controlling the light source driver 72 to turn on/off the laser light source 71. The drive controller 73 controls the timing for the light source driver 72 to supply power to the laser light source 71 based on an instruction signal from the input unit 74. The input unit 74 is realized with the used of, for example, a foot switch. When the foot switch is pressed, the input unit 74 accepts input of an instruction to emit the laser light and outputs the instruction signal to the drive controller 73 in accordance with the accepted input of the instruction.

The laser control device 7 is also connected to the processing device 4a. For example, when the drive controller 73 controls the light source driver 72 to turn on the laser light source 71, the laser control device 7 inputs, to the processing device 4a, a signal indicating that the laser light source 71 is turned on.

In the processing device 4a, in response to the signal being input from the laser control device 7, the observation mode setting unit 409 changes the observation mode from the normal observation mode to the laser light observation mode. When a treatment is performed using the laser light, for example, in a case where the laser light containing light in a wavelength band included in the green wavelength band is used, an operator such as a medical doctor wears goggles that cut the light in the wavelength band of the laser light. In the laser light observation mode, therefore, the interest color is set to a color component other than the color component corresponding to the wavelength band of the laser light, the color component including the wavelength band of the laser light is controlled so as not to be settable as the interest color, or the LED light source corresponding to the color component including the wavelength band of the laser light is set to be turned off. Alternatively, a color matrix may be changed after the white balance process in accordance with the wavelength band of the laser light. In the second embodiment, the control unit 408 functions as a laser sensing unit.

In a case where the processing device 4a and the laser control device 7 are not connected to each other, for example, the operator may input a change instruction signal for the observation mode to the processing device 4a by pressing a switch allocated to the operating unit 22 or the like of the endoscope 2 in accordance with the input operation for the input unit 74, and the observation mode setting unit 409 may change the observation mode in accordance with the change instruction signal.

According to the above-mentioned second embodiment, the effect similar to that of the first embodiment is obtained, and the change of the interest color and the operation control for the LED light source are performed by changing the observation mode when the laser light is used. Therefore, when the laser light is used, the trouble of manually changing the observation mode by the operator is saved, unnecessary emission of the light in the wavelength band which is likely to be cut by the goggles or the like is suppressed, and light other than the light in the wavelength band which is likely to be cut is set as the interest color. Consequently, unnecessary procedures related to the observation with the use of the goggles can be eliminated, and a clearer observation can be performed.

The first and second embodiments have been described on the premise that the red LED light source 311, the green LED light source 312, and the blue LED light source 313 are used as the light source unit 31a. However, an LED light source that emits light in a wavelength band other than red, green, and blue may be used, or a laser diode may be used as the light source.

According to some embodiments, the effect of being capable of suppressing the amount of heat generation and increasing the light quantity of a color component of interest can be obtained.

Additional advantages and modifications will readily occur to those skilled in the art. Therefore, the disclosure in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An imaging device comprising:
   an image sensor configured to capture an imaging object and output an imaging signal;
   a light source configured to emit respective beams of light of a plurality of colors of wavelength bands different from one another; and
   a processor comprising hardware, wherein the processor is configured to:
   separate the imaging signal into a plurality of signals corresponding to the plurality of colors;
   multiply each of the plurality of signals by a coefficient to perform a white balance adjustment;
   set a color corresponding to a wavelength band of interest as an interest color;
   control a light quantity of the interest color;
   compute a detection value ratio that is a ratio between a detection value of a signal corresponding to an interest color set and a detection value of a signal of another color corresponding to a wavelength band different from the wavelength band corresponding to the interest color among the plurality of signals where each is multiplied by the coefficient;
   calculate a coefficient ratio that is a ratio between a coefficient by which a signal corresponding to an interest color set is multiplied to perform the white balance adjustment and a coefficient by which a signal of another color corresponding to a wavelength band different from the wavelength band corresponding to the interest color is multiplied to perform the white balance adjustment;
   change a ratio between the coefficient by which the signal corresponding to the interest color is multiplied to perform the white balance adjustment and the coefficient by which the signal of the other color is multiplied to perform the white balance adjustment, based on the coefficient ratio calculated and on the detection value ratio computed; and
   change a light emission ratio between light corresponding to the interest color and light of the other color, based on the coefficient ratio calculated and on the detection value ratio computed, and output a control signal for emitting the respective beams of light of the plurality of colors by the changed light emission ratio.

2. The imaging device according to claim 1, wherein the plurality of colors is red, green, and blue.

3. The imaging device according to claim 1, wherein the processor is configured to:
   access a storage configured to store a first threshold value related to the coefficient ratio and a second threshold value related to the detection value ratio;
   perform control to reduce the coefficient ratio when the coefficient ratio calculated is greater than the first threshold value stored in the storage; and
   perform control to increase the light emission ratio when the detection value ratio computed is greater than the second threshold value stored in the storage.

4. The imaging device according to claim 1, wherein the processor is configured to:
   sense that laser light has been emitted from a laser device capable of emitting the laser light; and
   set to an observation mode in which the interest color set is set to a color component other than a color component corresponding to a wavelength band of the laser light when the laser light has been sensed.

5. A processing device connected to an image sensor and a light source, the image sensor being configured to capture an imaging object and output an imaging signal, the light source being configured to emit respective beams of light of a plurality of colors of wavelength bands different from one another, wherein the processing device comprises:
   a processor comprising hardware, wherein the processor is configured to:
      send and receive a signal between the image sensor and the light source;
      multiply a plurality of signals by a coefficient to perform a white balance adjustment, the plurality of signals being obtained by separating the imaging signal in accordance with the plurality of colors;
      set a color corresponding to a wavelength band of interest as an interest color;
      compute a detection value ratio that is a ratio between a detection value of a signal corresponding to an interest color set and a detection value of a signal of another color corresponding to a wavelength band different from the wavelength band corresponding to the interest color among the plurality of signals where each is multiplied by the coefficient;
      calculate a coefficient ratio that is a ratio between a coefficient by which a signal corresponding to an interest color set is multiplied to perform the white balance adjustment and a coefficient by which a signal of another color corresponding to a wavelength band different from the wavelength band corresponding to the interest color is multiplied to perform the white balance adjustment;
      change a ratio between the coefficient by which the signal corresponding to the interest color is multiplied to perform the white balance adjustment and the coefficient by which the signal of the other color is multiplied to perform the white balance adjustment, based on the coefficient ratio calculated and on the detection value ratio computed; and
      change a light emission ratio between light corresponding to the interest color and light of the other color, based on the coefficient ratio calculated and on the detection value ratio computed, and output, to the light source, a control signal for emitting the respective beams of light of the plurality of colors by the changed light emission ratio.

6. The imaging device according to claim 1, wherein the processor is configured to:
   sense that laser light has been emitted from a laser device capable of emitting the laser light; and
   set to an observation mode in which an emission of light of a color component corresponding to a wavelength band of the laser light is not performed by the light source when the laser light has been sensed.

* * * * *